United States Patent [19]
Rossmy

[11] 3,948,963
[45] Apr. 6, 1976

[54] EQUILIBRATED MIXTURES OF ORGANOPOLYSILOXANES CONTAINING SULFONIC ACID GROUPS AND PROCESS FOR THE PREPARATION OF SUCH ORGANOPOLYSILOXANES

[75] Inventor: Gerd Rossmy, Essen-Werden, Germany

[73] Assignee: Th. Goldschmidt AG, Essen, Germany

[22] Filed: May 22, 1974

[21] Appl. No.: 472,360

[30] Foreign Application Priority Data
June 22, 1973 Germany............................ 2331677

[52] U.S. Cl. 260/448.2 N; 260/448.2 E; 260/448.8 R
[51] Int. Cl.²............................................ C07F 7/08
[58] Field of Search.............. 260/448.2 N, 448.2 E

[56] References Cited
UNITED STATES PATENTS

| | | |
|---|---|---|
| 3,183,254 | 5/1965 | Rossmy et al................ 260/448.2 N |
| 3,488,372 | 1/1970 | Rossmy et al................ 260/448.2 N |
| 3,595,885 | 7/1971 | Rossmy et al............ 260/448.2 E X |
| 3,652,624 | 3/1972 | Rossmy....................... 260/448.2 N |
| 3,655,712 | 4/1972 | Rossmy....................... 260/448.2 N |

*Primary Examiner*—Paul F. Shaver
*Attorney, Agent, or Firm*—Toren, McGeady and Stanger

[57] ABSTRACT
The disclosed equilibrated mixtures of organopolysiloxanes containing sulfonic acid groups have the average unit formula

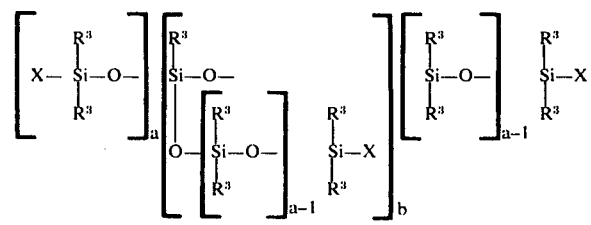

In this formula, $b$ has a value of from 0 to 50, preferably 0 to 10;

$a$ is a numeral which is selected so that the average unit molecule comprises 2 to 100, preferably 4 to 50 silicon atoms and the ratio of $R^3$ groups which are not linked to trifunctional Si-atoms to $R^3$ groups which are linked to trifunctional Si-atoms is at least 4;

$R^3$ is alkyl, substituted alkyl, aryl or substituted aryl; and

X is halogen,

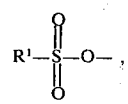

wherein $R^1$ is alkyl, aryl or alkaryl, or

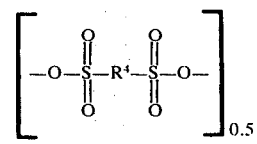

wherein $R^4$ is divalent hydrocarbon, at least 3% of X constituting said

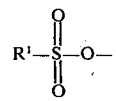

or

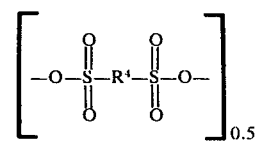

groups, the number of said

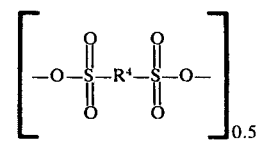

groups in the unit not exceeding 10.

The novel equilibrated mixtures of sulfonic acid groups containing organopolysiloxanes may be directly used as equilibration and polymerization catalysts for organopolysiloxane systems. They also serve as intermediaries in the production of foam stabilizers. Numerous other uses for the novel compounds are disclosed in the application.

25 Claims, No Drawings

EQUILIBRATED MIXTURES OF ORGANOPOLYSILOXANES CONTAINING SULFONIC ACID GROUPS AND PROCESS FOR THE PREPARATION OF SUCH ORGANOPOLYSILOXANES

The invention also discloses a process of preparing equilibrated mixtures of organopolysiloxanes containing organosulfonic acid groups linked to silicon, according to which organohalogensilanes are reacted with water in an amount insufficient to split off all the halogen groups and with organosulfonic acid in amounts of 0.005 to 1 val/mol silane.

FIELD OF INVENTION

The invention is directed to organopolysiloxanes and more particularly to equilibrated mixtures of organopolysiloxanes containing organosulfonic acid groups linked to silicon.

Considered from another aspect, the invention deals with a procedure for the preparation of equilibrated organopolysiloxane mixtures containing organosulfonic acid groups linked to silicon.

BACKGROUND INFORMATION AND PRIOR ART

Organopolysiloxanes with terminal reactive groups have considerable technical and industrial importance. Of particular interest from a practical point of view are such siloxanes which are equilibrated by the incorporation of sulfate groups into the siloxane structure. The term "equilibration" in this context refers to the equilibrium adjustment of the polysiloxane mixture in respect of the molecular weight distribution and the distribution of the different organosiloxane units which may be present within the molecule. The sulfate groups which are incorporated into the siloxane structure may also take over the function of a terminal reactive group. The chemical literature, including the patent literature, contains ample references to such systems. Examples are German Offenlegungsschrift No. 2 059 546 and German Offenlegungsschrift No. 2 059 554, to which particular attention is directed.

German Offenlegungsschrift No. 2 059 546 is directed to a procedure for the preparation of predominantly linear equilibrated organopolysiloxane mixtures containing terminal sulfuric acid groups. The equilibrated organopolysiloxane mixtures of the German Offenlegungsschrift can be represented by the general formula

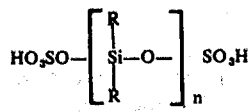  I

In this formula, the letter *n* stands for a value of 2 to 20 while R is a hydrocarbon group which in some cases may be substituted by a group which is inert to sulfuric acid. A portion of the hydrocarbon groups R may be replaced by the group

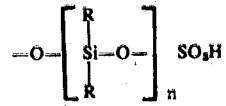

The substances of formula I above are in equilibrium with cyclic compounds of the general formula

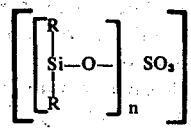  II and sulfuric acid.

IN formula II above, R has the above indicated meaning while two of the groups

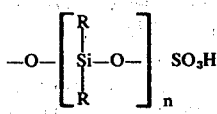

may be replaced by one group

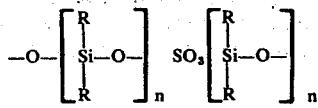

In formula II, *m* has a value of from 1 to 10, preferably 1 or 2.

The subject matter of Offenlegungsschrift No. 2 059 554, as mentioned above, is a process for the preparation of equilibrated mixtures of polydiorganosiloxanylsulfates of the general formula

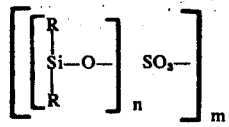

In this formula, n has a value of 2 to 20, preferably 2 to 10, while m has a value of 1 to 10, preferably 1 to 2; the R groups may be the same or different and indicate lower alkyl of preferably 1 or 2 carbon atoms which, if desired, may be substituted. A portion of the R groups may be replaced by aromatic groups, preferably by phenyl, or by the group

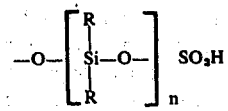

According to the Offenlegungsschrift, two of the R groups may be relaced inter- or intramolecularly by one group

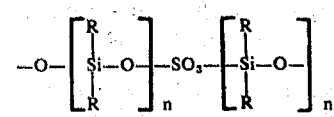

Of particular interest in this context are those organopolysiloxanes which, in addition to the siloxanyl sulfate groups, also contain terminal silylhalide groups, particularly silylchloride groups. The production of such compounds has been disclosed, for example, in German Pat. No. 1 174 509 and in U.S. Pat. No. 3,115,512. The presence of the siloxanyl sulfate groups assures the rapid and finite formation of the equilibration condition. Compounds of the nature referred to above are widely used starting compounds for numerous reactions. Thus, for example, they are used as starting compounds in the production of polysiloxanes with terminal hydroxyl groups or of polyalkyl silicic acid esters, of polysiloxanes with acyloxy alkyl groups and the like. They also serve as the organosilicon starting compounds for the modification of, for example, epoxy resins.

Of particular interest from a practical point of view are the reactions with higher molecular hydroxyl compounds for the production of polysiloxane-polyoxyalkylene-mixed block polymers as, for example, disclosed in the aforementioned U.S. Pat. No. 3,115,512. In such reactions, a tendency to side reactions can be observed. This tendency has is genesis in the reaction of the liberated sulfuric acid with the organic hydroxyl compounds under formation of sulfuric acid esters. This side reaction can be retarded and negated by the use of acid acceptors. However, from a practical point of view, it has been observed that in many instances and in spite of the use of acid acceptors, precipitation of small amounts of byproducts takes place.

SUMMARY OF THE INVENTION

It is a primary object of the present invention to provide an equilibrated organopolysiloxane mixture which contains reactive groups which can take over the role of the prior art intramolecular or terminal sulfate groups which are linked to one or several silicon atoms, but which do not exhibit the disadvantages of such sulfate groups. This means that the reactive groups which are proposed by this invention have to have the same equilibrating action as the prior art siloxanyl sulfate groups without, however, causing directly or indirectly the occurrence of undesired side reactions.

It is also an object of the present invention to provide polysiloxane systems of the indicated kind which have a wide utility of the nature of the prior art compounds.

It is also a object of the present invention to propose a procedure for preparing such reactive group containing polysiloxane systems in a simple and relatively inexpensive manner.

Briefly, and in accordance with the invention, novel equilibrated mixtures of organopolysiloxanes have the average unit formula

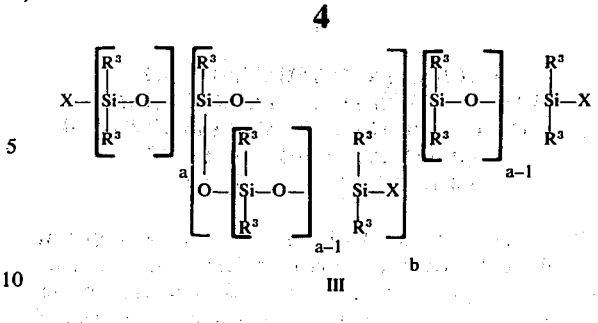

III

In this formula, b has a numerical value of from 0 to 50, preferably 0 to 10; a is a numeral which is selected so that the average unit molecule comprises 2 to 100, preferably 4 to 50 silicon atoms, the ratio of $R^3$ groups which are not linked to trifunctional Si-atoms to $R^3$ groups which are linked to trifunctional Si-atoms being at least 4; $R^3$ is alkyl, substituted alkyl, aryl or substituted aryl. From a practical point of view $R^3$ is predominantly methyl. However, within the molecule $R^3$ can also, at least partially, have the meaning of a different alkyl or aryl group which may be substituted and which, of course, should be inert in respect of acid. Such groups are, for example,

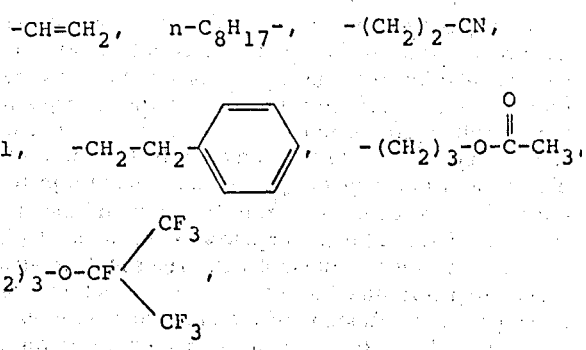

or —$(CH_2)_3$—O—alkyl. The $R^3$ group which is formally linked to the trifunctional silicon atom, may in its entirety or partially have the meaning of —$O_{0.5}$—, the group having an intra- or intermolecular linking action. In the latter case, the molecule thus also contains tetrafunctional silicon atoms.

X stands for halogen, preferably chlorine, or the group

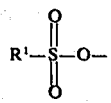

wherein $R^1$ is alkyl, aryl or aralkyl.

In the average molecule, at least 3 percent and preferably 20 percent or more of all the X groups should correspond to the group

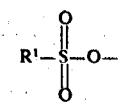

As a matter of fact, it is even feasible that all the X groups are constituted by

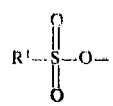

A portion of the X groups, however, may also be triorganosiloxy, preferably trimethylsiloxy, dependent on the relatively small amount of mono-functional organosilanes which may be present in the halogen mixture.

X, however, can also stand for

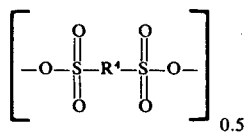

wherein R⁴ is divalent hydrocarbon. However, the number of such

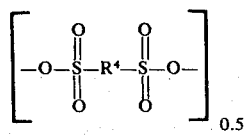

groups in the average molecule should not exceed 10.

However, it is certainly feasible and within the scope of the present invention, to use organosulfonic acids wherein $R^1$ constitutes a divalent group, which contains an additional $SO_3H$ group. Examples for such disulfonic acids are, for example, naphthalinedisulfonic acids, 4,4'-diphenyldisulfonic acid and α,Φ-alkanedisulfonic acids.

In the latter instance the disulfonic acid links the polysiloxane blocks intermolecularly or intramolecularly.

In respect of the silanes to be reacted in accordance with the inventive process, mono, di, tri and tetrafunctional halogensilanes may be employed, such as, for example, $R^3SiX_3$, $R_2^3SiX_2$, $SiX_4$ and $R_3^3SiX$. The latter are used in small amounts as terminal groups. The X in the halogensilanes referred to stands for a halogen atom, preferably chlorine. As indicated in conjunction with the definition of the inventive polysiloxane mixture, $R^3$ is predominantly methyl which, however, partially may have the meaning of another alkyl or aryl group which may be substituted and which should be inert to acid. Such groups are, for example,

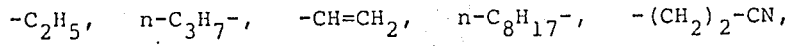

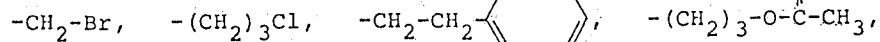

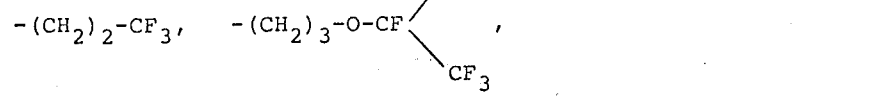

The divalent hydrocarbon of R⁴ is preferably an alkylene of preferably 2 to 18 carbon atoms. R⁴ may, however, also be arylene, such as phenylene, napthylene or 4,4'-diphenylenemethane. The valences in the formula which are shown in free condition become saturated by intermolecular or intramolecular linking.

The inventive procedure for preparing such organosulfonic acid group containing polysiloxane mixtures of equilibrated nature provides that organohalogensilanes or mixtures thereof are reacted with an amount of water which is insufficient to split off all the halogen groups and with organosulfonic acid in amounts of 0.005 to 1 val/mole silane.

The process for preparing the inventive compounds proceeds analogous to the preparation of the siloxanyl sulfates as disclosed in German Pat. No. 1 174 509.

The organosulfonic acids which are reacted with the organohalogensilanes may correspond to the formula

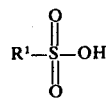

wherein $R^1$ has the above-indicated meaning, to wit, stands for alkyl, aryl or alkaryl. Particularly preferred groups of this nature are alkyls, such as methyl, ethyl, propyl, isopropyl, butyl and isobutyl. In respect of aryl groups, phenyl is the most preferred one. Concerning the alkaryl groups, p-toluolyl and p-dodecylphenyl are recommended.

or —(CH₂)₃—O—alkyl.

A detailed disclosure in respect of substituents in organopolysiloxanes which are inert in respect of acid and which can be equilibrated with acid catalysts, is contained in the book by W. Noll "Chemie und Technologie der Silicone", Verlag Chemie GmbH, 1968, as well as in U.S. Pat. No. 3,115,512 previously referred to.

It is of particular advantage if the inventive procedure is carried out in two stages.

The first stage then consists in partially hydrolyzing the silane mixture to form a mixture of siloxanes. The mixture still contains siloxanes which comprise terminal halogen groups.

The second stage resides then in the reaction of this mixture with the organosulfonic acid which, under equilibration, is incorporated into the siloxane system. In case monosulfonic acid is used, the sulfonic acid group is then in terminal position.

The preferred reaction temperature abounts to about 10° to 100°C. The hydrogenhalide can be completely removed at the end of the reaction, for example, by suitable evacuation.

The quantity of organosulfonate groups which is built into the polysiloxane molecule, is dependent on the desired speed of the equilibration reaction and also on the constitution of the siloxane to be equilibrated. Branched siloxanes require generally a slightly higher amount of sulfonic acid. Generally, satisfactory results are obtained if, per mole of siloxane linkage, at least 0.005 val, preferably 0.02 val of organosulfonic acid are used. The term "val" means in this context mole/-valence.

The modified siloxanes obtained in accordance with the invention have the advantage of exhibiting reduced viscosity if monosulfonic acids are used. In a preferred embodiment of the invention monosulfonic acids are employed.

The structure of the sulfonic acid group containing polysiloxane mixtures obtained in accordance with the invention, has previously been indicated. It should be emphasized, however, that the formula given refers to an average formula which characterizes the equilibrated mixture.

Equilibrated polysiloxane mixtures of specific nature which can be obtained by the inventive procedure may be represented by the following average formulas:

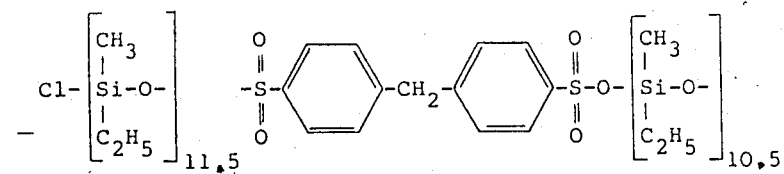

perature. The mixture was thereupon heated at 18 mm Hg (Torr) for one hour at 40°C. A clear liquid resulted which upon titration exhibited $1.9 \cdot 10^{-3}$ (theoretical $1.83 \cdot 10^{-3}$) val acid/g of product.

The inventive product obtained corresponds to the formula III above with the following parameters:
$a = 3$;
$b$ O; O;
$R^3 = CH_3$;
$x =$

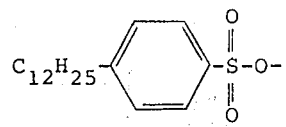

In order to investigate the equilibration condition, the liquid was reacted with methanol in the presence of triethylamine as acid acceptor. 82 percent of the resulting reaction product ($\alpha,\Omega$-methoxysiloxane) could be removed by distillation at a bath temperature of 300°C

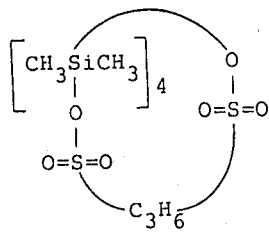

and a pressure of 0.2 mm Hg (Torr). In the gas-chromatogram, linear methoxysiloxanes and cyclic polydimethylsiloxanes were detected. The following Table indicates the surface portions for the individual species. For comparison purposes, the data of methoxysiloxane which was obtained from a chlorosiloxane of comparable chain length and which was equilibrated by incorporation of sulfate groups, are also shown in the Table, without, however, in each instance considering the correction factor for the total siloxane.

The invention will now be described by several Examples, it being understood, however, that these Examples are given by way of illustration and not by way of limitation and that many changes may be effected without affecting in any way the scope and spirit of the invention as recited in the appended claims.

EXAMPLE 1

By partial hydrolysis of dimethyldichlorosilane, a siloxane mixture was obtained which contained about 50% of cyclic polydimethylsiloxane of the average gross formula

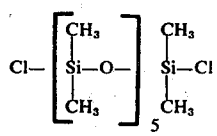

One mole of this product was treated with two mole of dodecylbenzenesulfonic acid for 5 hours at room tem- Table

| Linear $\alpha,\omega$-methoxy polydimethylsiloxane chain length | Inventive Product peak-area-% | Comparison Product peak-area-% |
|---|---|---|
| 3 | 3.2 | 9.7 |
| 4 | 9.0 | 10.6 |
| 5 | 10.0 | 9.6 |
| 6 | 9.9 | 8.4 |
| 7 | 9.2 | 7.5 |
| 8 | 8.4 | 6.7 |
| 9 | 7.4 | 6.1 |
| 10 | 6.7 | 5.2 |
| 11 | 5.5 | 4.9 |
| 12 | 4.3 | 4.0 |
| 13 | 2.7 | 3.4 |

The moiety of cyclic products amounts in the inventive product to 3.2 peak-area-%, while in the comparison product the value is 3.4 peak-area-%. The distribution curves conform to equilibrated systems. The differences between the inventive product and the comparison product in the range of small chain lengths, presumably express a specific influence of the chain limiting groups.

EXAMPLE 2

Preparation of an equilibrated mixture of the formula

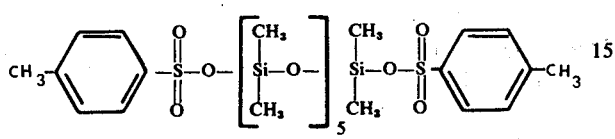

1 mole of the non-equilibrated chlorosiloxane mixture of Example 1 was reacted for 3 hours at 20°C with 2 mole of p-toluenesulfonic acid. After evacuation for 8 hours (17 Torr) a chlorine-free liquid was obtained containing $2.70 \cdot 10^{-3}$ val acid/g of product (theoretical $2.6 \cdot 10^{-3}$). After the conversion which was carried out in a manner analogous to that disclosed in Example 1, to form a $\alpha$ $\Omega$-methoxysiloxane, gaschromatographic analysis indicates a chain length distribution which is very similar to that of the inventive product of Example 1.

EXAMPLE 3

A non-equilibrated organopolysiloxane mixture of the general formula

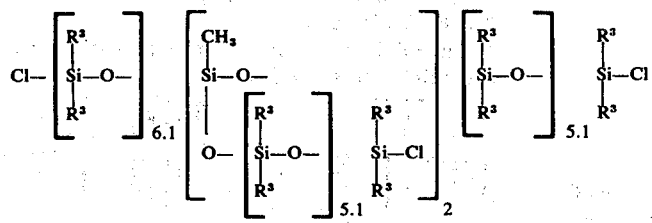

was used as starting material. In this formula, 12.5% of $R^3$ is made up of —$(CH_2)_3$—Cl while 87.5% consists of $CH_3$. Exclusively,

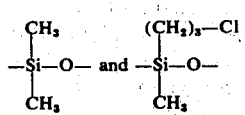

structures were present. This mixture was obtained by reaction of the corresponding silane with an insufficient amount of $H_2O$. This non-equilibrated organopolysiloxane mixture was equilibrated by reaction with 0.85 mole of ethanesulfonic acid/mole siloxane mixture. The sulfonic acid was built in into the siloxane structure under evolvement of HCl. After evacuation at 50°C, the siloxane mixture which is now equilibrated, was reacted in a toluene solution (3 liters of toluene/kg of reaction partner) with a polyether-monool mixture and i-propanol. The polyether-monool mixture was obtained by an addition reaction of 57% by weight of propyleneoxide and 43% by weight of ethyleneoxide to n-butanol and has secondary OH groups and an average molecular weight of 2,450. (0.90 mole of polyether and 0.17 mole of i-propanol/val acid in the equilibrated mixture.) Ammonia was used as acid acceptor. The product was stabilized by the addition of 0.4% by weight of ethanolamine.

The formula of the inventive product of Example 3 corresponds to the formula III with the following parameters:
$a = 6.1$;
$b = 2$;
$R^3 = 12.5\%$ $(CH_2)_3$—Cl and $87.5\%$ $CH_3$ in form of

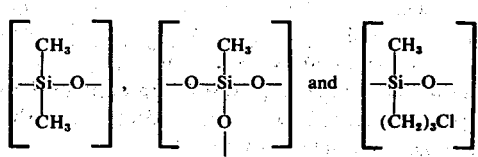

-structures X = 21.2%

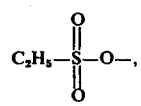

78.8% Cl

The resulting product is an excellent foam stabilizer for polyether-polyurethane foams. The product is comparable with a product which is obtained from a chlorosiloxane which is equilibrated by incorporation of sulfate groups. The activity as foam stabilizer is a clear indication that equilibration of the siloxane had occurred. Similar results are obtained if the $CH_3Si[(CH_2)_3Cl)]Cl_2$ in the starting silane mixture is replaced by equivalent amounts of acetoxypropylmethyldichlorosilane, propylmethyldichlorosilane, octylmethyldichlorosilane and phenylmethyldichlorosilane. All the foam stabilizers here disclosed are suitable particularly for flame protected soft foam systems.

EXAMPLE 4

The Cl-siloxane mixture of Example 1 is equilibrated by reaction with 0.2 mole of methanesulfonic acid/mole of siloxane for 3 hours at 20°C and for 1 hour at 50°C and 20 Torr. The equilibration which took place can be detected in the gaschromatographically established distribution of the $\alpha,\Omega$-methoxydiloxane which is obtained by reaction with methanol. By comparison (see the Table below), methoxysiloxane from the same starting siloxane was equilibrated by adding 0.1 mole of $H_2SO_4$/mole siloxane.

Table

| Chain Length of α,ω-Methoxypoly-dimethylsiloxane | Inventive Product peak-area-% | Comparison Product peak-area-% |
|---|---|---|
| 1 | 1.0 | 0.8 |
| 2 | 6.1 | 3.8 |
| 3 | 12.1 | 9.5 |
| 4 | 14.1 | 11.7 |
| 5 | 11.7 | 10.8 |
| 6 | 10.3 | 9.9 |
| 7 | 8.6 | 8.5 |
| 8 | 7.1 | 7.3 |
| 9 | 5.7 | 6.4 |
| 10 | 4.6 | 5.5 |
| 11 | 3.8 | 4.6 |
| 12 | 2.9 | 3.8 |
| 13 | 2.2 | 3.0 |

The moiety of cyclic products amounts in the inventive product accordingly to 3.4 percent while the comparison product had 4.5 percent.

The product of Example 4 corresponds to formula III with the following parameters:

$a = 3; b = 0, R^3 = CH_3;$ $X = 10\%$

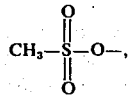

90% Cl

EXAMPLE 5

1 mole of a non-equilibrated linear siloxane of the gross formula

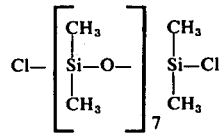

is equilibrated with 0.266 mole of methanesulfonic acid and - another batch for comparison purposes - with 0.133 mole of H₂SO₄, respectively, for 5 hours at 20°C and for 2 hours at 100°C. The reaction products thus obtained were reacted with 1.1 mole of a polyether-monool which in turn was obtained by addition of propyleneoxide to n-butanol with an average mole weight of 372 (2 l of toluene/reaction product; acid acceptor: triethylamine). Both products thus obtained exhibited good cell regulating activity in so-called cold foam polyurethane formulations on the basis of polyethers, cross-linking agents and higher functional isocyanates (toluylenediisocyanate, polymeric MDI; available on the market, for example, under the trade name crude TDI, Desmodur 44 V). In respect of the product which has been obtained from the Cl-siloxane equilibrated with the H₂SO₄, storage of the product resulted in a gradual separation of a second liquid phase. By contrast, the equilibrated siloxane prepared in accordance with the invention resulted in a clear one-phase product and no separation took place.

The inventive product of Example 5 corresponds to formula III with the following parameters:

$a = 4; b = 0; R^3 = CH_3;$ $X = 13.3\%$

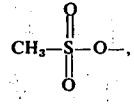

86.7% Cl

It should be observed that the formulas referred to in the Examples are directed to and depict the sulfonic acid group containing organopolysiloxanes and not to the further processed products. The percent indication of the symbols in each instance refers to mole percent.

It will be appreciated from the above that the inventive products are not foam stabilizers per se, but foam stabilizers may easily be obtained from the products, for example, if they are employed as intermediaries in the manner disclosed, for example, in Example 3. The inventive products may be used for the same purpose as the prior art compounds referred to in the introductory portion of this application, to wit, the siloxanyl sulfate group containing polysiloxane. They may also be directly used as equilibration and polymerization catalysts for organopolysiloxane systems.

What is claimed is:

1. An equilibrated mixture of organopolysiloxanes of the average unit formula

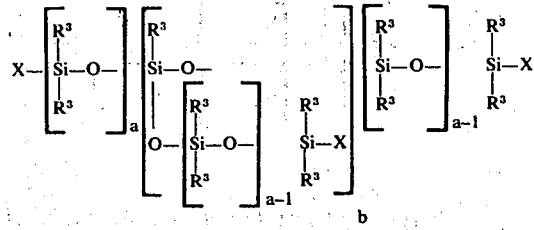

wherein:

$b = 0 - 50$;

$a$ is a numeral which is selected so that the average unit molecule comprises 2 – 100 silicon atoms and the ratio of $R^3$ groups which are not linked to trifunctional Si-atoms to $R^3$ groups which are linked to trifunctional Si-atoms is at least 4;

$R^3$ is alkyl, substituted alkyl selected from the group consisting of

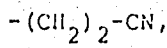

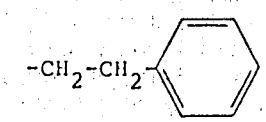

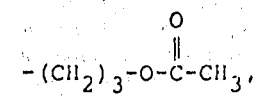

and —$(CH_2)_3$—O—alkyl, vinyl, or aryl and X is halogen,

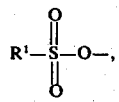

wherein $R^1$ is alkyl, aryl or alkaryl, or

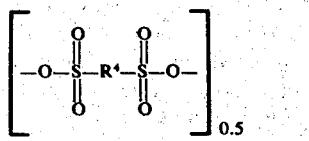

wherein $R^4$ is divalent hydrocarbon, at least 3% of X constituting said

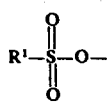

or

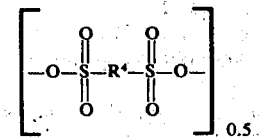

groups, the number of said

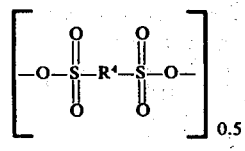

groups in the unit not exceeding 10, and a portion of X may be trialkylsiloxy and wherein the free valences are saturated by intermolecular or intramolecular linking.

2. The mixture of claim 1, wherein $b = 0 -10$.

3. The mixture of claim 1, wherein a is selected so that the average unit molecule comprises 4 –50 silicon atoms.

4. The mixture of claim 1, wherein $R^3$ is methyl.

5. The mixture of claim 1, wherein $R^3$ is a group which is inert in the presence of acids and is alkyl, substituted alkyl, or aryl.

6. The mixture of claim 5, wherein $R^3$ is one or more selected from the group consisting of

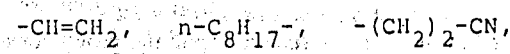

and —$(CH_2)_3$—O—alkyl.

7. The mixture of claim 1, wherein the $R^3$ which is linked to the trifunctional Si-atom is at least partially —O—$_{0.5}$ 8. The mixture of claim 1, wherein $R^4$ is alkylene of 2 – 18 carbon atoms or arylene.

9. The mixture of claim 8, wherein the arylene is phenylene, naphthylene or 4,4'-diphenylenemethane.

10. The mixture of claim 1, wherein said halogen is chlorine.

11. The mixture of claim 1, wherein $R^1$ is methyl, ethyl, propyl, isopropyl, butyl, isobutyl, phenyl, p-toluolyl or p-dodecylphenyl.

12. The mixture of claim 1, wherein at least 20% of X are

groups.

13. The mixture of claim 1, wherein X is entirely constituted of

groups.

14. The mixture of claim 1, wherein a portion of the X-groups are trialkylsiloxy groups.

15. The mixture of claim 14, wherein the trialkylsiloxy is trimethylsiloxy.

16. An equilibrated mixture of organopolysiloxanes of the average unit formula

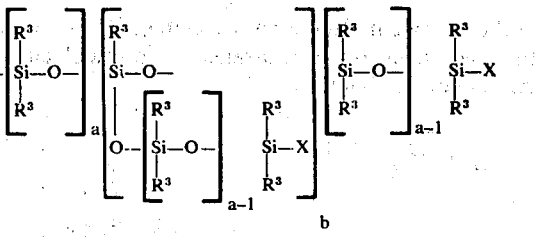

wherein:
$b = 0 - 10$;

a is a numeral which is selected so that the average unit molecule comprises 4 – 50 silicon atoms and the ratio of $R^3$ groups which are not linked to trifunctional Si-atoms to $R^3$ groups which are linked to trifunctional Si-atoms is at least 4;

$R^3$ is one or more selected from the group consisting of

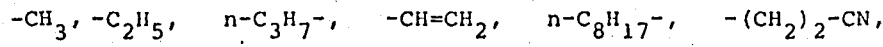

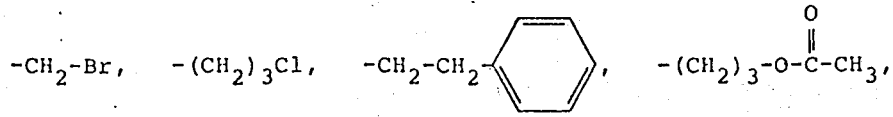

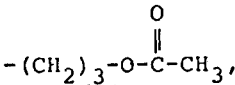

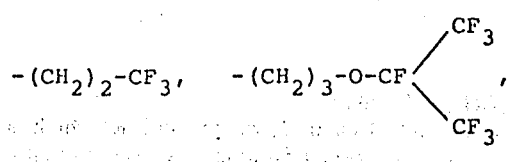

and $(CH_2)_3$—O—alkyl and
X is chlorine,

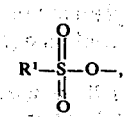

wherein $R^1$ is alkyl, aryl or aralkyl, or

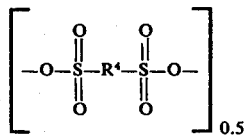

, wherein $R^4$ is alkylene of 2 – 18 carbon atoms, phenylene, napththylene or 4,4'-diphenylenemethane, at least 20% of X being said

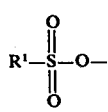

and the number of

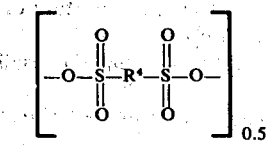

in the average molecule not exceeding 10 and wherein the free valences are saturated by intermolecular or intramolecular linking.

17. A process of preparing equilibrated organopolysiloxane mixtures of claim 1 having organosulfonic acid groups linked to silicon, which comprises reacting organohalogensilanes or mixtures thereof which are convertible into said polysiloxanes with a. an amount of water which is insufficient to split off all halogen groups and b. organosulfonic acid in amount of 0.005-1 mole/valence silane.

18. A process as claimed in claim 17, wherein the organohalogensilane or the mixtures thereof are first partially hydrolyzed with an amount of $H_2O$ which is insufficient for splitting off all halogen groups, whereupon the organopolysiloxane thus obtained and which comprises terminal halogen groups is reacted with said organosulfonic acid.

19. A process as claimed in claim 16, wherein said organohalogensilanes are organochlorosilanes.

20. A process as claimed in claim 17, wherein said organosulfonic acid corresponds to the formula

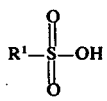

wherein $R^1$ is alkyl, aryl or alkaryl.

21. A process as claimed in claim 20, wherein $R^1$ is alkyl of 1 to 4 carbon atoms, phenyl, p-toluoyl or p-dodecylphenyl.

22. A process as claimed in claim 17, wherein said organosulfonic acid is a disulfonic acid which links the polysiloxane blocks with each other.

23. An equilibrated mixture of organopolysiloxanes of the average unit formula

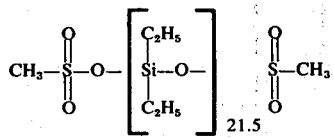

24. An equilibrated mixture of organopolysiloxanes of the average unit formula

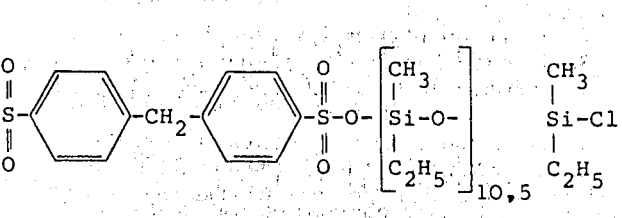

25. An equilibrated mixture of organopolysiloxanes of the average unit formula
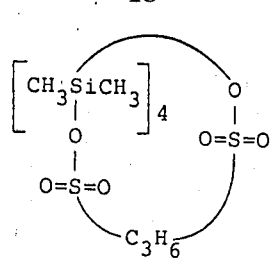
* * * * *